(12) United States Patent
Xu et al.

(10) Patent No.: US 11,732,196 B2
(45) Date of Patent: Aug. 22, 2023

(54) METHOD FOR UPGRADING PYROLYSIS OIL THROUGH SEAWATER ELECTROCHEMICAL PRETREATMENT OF BIOMASS FEEDSTOCK

(71) Applicant: South China Agricultural University, Guangzhou (CN)

(72) Inventors: Xiwei Xu, Guangzhou (CN); Haipeng Yu, Qingdao (CN); Enchen Jiang, Qingdao (CN); Fan Zhang, Guangzhou (CN); Linghao Li, Guangzhou (CN); Hong Wang, Guangzhou (CN); Yan Sun, Guangzhou (CN)

(73) Assignee: SOUTH CHINA AGRICULTURAL UNIVERSITY, Guangzhou (CN)

( * ) Notice: Subject to any disclaimer, the term of this patent is extended or adjusted under 35 U.S.C. 154(b) by 0 days.

(21) Appl. No.: 17/851,952

(22) Filed: Jun. 28, 2022

(65) Prior Publication Data
US 2023/0159831 A1 May 25, 2023

(30) Foreign Application Priority Data
Nov. 22, 2021 (CN) .......................... 202111382561.9

(51) Int. Cl.
*C10B 53/02* (2006.01)
*C10B 57/08* (2006.01)
(Continued)

(52) U.S. Cl.
CPC ............ *C10B 57/08* (2013.01); *C07D 307/46* (2013.01); *C10B 53/02* (2013.01); *C10G 1/042* (2013.01);
(Continued)

(58) Field of Classification Search
None
See application file for complete search history.

(56) References Cited

U.S. PATENT DOCUMENTS

2017/0159076 A1* 6/2017 Bathula .................... C08H 8/00

FOREIGN PATENT DOCUMENTS

| CN | 109650388 A | * | 4/2019 |
| CN | 111057568 A | * | 4/2020 |

(Continued)

OTHER PUBLICATIONS

PE2E translation of DD-223175-A1.*
(Continued)

*Primary Examiner* — Jonathan Luke Pilcher
(74) *Attorney, Agent, or Firm* — McDonnell Boehnen Hulbert & Berghoff LLP

(57) ABSTRACT

Provided is a method for upgrading pyrolysis oil through seawater electrochemical pretreatment of biomass and use thereof. The method includes: (1) crushing and sieving a biomass raw material to obtain a crushed biomass raw material, adding the crushed biomass raw material to a salt solution and mixing to be uniform to obtain a reactant mixture; performing an electrolytic reaction on the reactant mixture under conditions of stirring and an external voltage of 5-15 V for 2-8 hours to obtain a product mixture; after the electrolytic reaction, subjecting the product mixture to a suction filtration, collecting a filter cake, washing the filter cake and drying to obtain a pretreated biomass, and (2) subjecting the pretreated biomass obtained in step (1) to a pyrolysis reaction at a temperature of 400-600° C. for 30-90 minutes in a protective gas atmosphere, and collecting a pyrolysis oil by an organic solvent.

9 Claims, 9 Drawing Sheets

(51) Int. Cl.
*C10G 1/04* (2006.01)
*C07D 307/46* (2006.01)
*C10G 32/02* (2006.01)

(52) U.S. Cl.
CPC ..... *C10G 32/02* (2013.01); *C10G 2300/1014* (2013.01)

(56) References Cited

FOREIGN PATENT DOCUMENTS

| CN | 111943917 A | * | 11/2020 |
| CN | 112899067 A | * | 6/2021 |
| CN | 113416565 A | * | 9/2021 |
| CN | 113862015 A | * | 12/2021 |
| DE | 223175 A1 | * | 5/1985 |

OTHER PUBLICATIONS

PE2E translation of CN-109650388-A.*
PE2E translation of CN-113862015-A.*
PE2E translation of CN-111057568-A.*
PE2E translation of CN-111943917-A.*
PE2E transatlion of CN-112899067-A.*
PE2E translation of CN-113416565-A.*

* cited by examiner

METHOD FOR UPGRADING PYROLYSIS OIL THROUGH SEAWATER ELECTROCHEMICAL PRETREATMENT OF BIOMASS FEEDSTOCK

CROSS REFERENCE TO RELATED APPLICATION

This application claims the benefit and priority of Chinese Patent Application No. 202111382561.9, entitled "Method for upgrading pyrolysis oil through seawater electrochemical pretreatment of biomass and use thereof" filed on Nov. 22, 2021, the disclosure of which is incorporated by reference herein in its entirety as part of the present application.

TECHNICAL FIELD

The present disclosure relates to the technical field of biomass energy, and in particular to a method for upgrading pyrolysis oil through seawater electrochemical pretreatment of biomass and use thereof.

BACKGROUND ART

Lignocellulose, as a renewable, green and sustainable resource, is considered as one of the alternative sources of fossil energy, and could produce high-value chemicals and pharmaceutical additives. Pyrolysis is considered to have low economic investment and high liquid yield, and is the most effective way to convert lignocellulose into chemical products. However, a pyrolysis oil generated by the pyrolysis is an extremely complicated mixture, composed of water and hundreds of organic oxygen compounds, such as furan, pyran, anhydrosugar and phenols. Among them, the produced levoglucose (LG) and furfural are promising bulk chemical reagents, which could be used as surfactants, plastics, medicines and resins. However, the pyrolysis oil has an extremely low concentration of LG and furfural, resulting in the problem of extraction and subsequent purification. In order to increase the content of LG and furfural, and reduce the synthesis cost of value-added chemicals in the midstream and downstream processes, it is necessary to adjust the composition and structure of the biomass through a pretreatment process.

Generally, methods of the pretreatment include a physical pretreatment, a chemical pretreatment, a physicochemical pretreatment, and a biological pretreatment. However, classic methods of pretreatment, such as a hydrothermal pretreatment, an acid pretreatment, and an alkali pretreatment, adopt harsh conditions, have difficulty in treating waste liquids, and are not environmentally friendly. Furthermore, an ionic liquid pretreatment and a deep eutectic solvent pretreatment are considered as green and environmentally friendly, but are limited by their high cost and immature recovery technologies. Therefore, developing an efficient, economical and green method of pretreatment remains a daunting challenge. For decades, an electrochemistry method has been recognized as an efficient way to degrade contaminants in water, selectively transform organics, and create corrosion-resistant materials. The unique ability of the electrochemistry to generate redox species or reactive intermediates under mild conditions opens up a new possibility for the separation of lignocellulose from biomass. During the electrochemical process, some components in the biomass are degraded through active intermediates, causing changes in composition and structure. Furthermore, it is attractive that the electrochemical pretreatment, as a means of separation of lignocellulose, makes it possible to additionally obtain a by-product with high commercial value (hydrogen gas). Therefore, the electrochemical pretreatment of biomass under mild conditions is a promising way.

In previous electrochemical pretreatment studies, electrolytes have a great influence on the electrochemical pretreatment of biomass. Maazuza et al. performed a pretreatment of biomass with ionic liquid as an electrolyte. For aqueous electrolytes, the role of an external voltage in the electrochemical pretreatment is determined by solutes. On the one hand, the external voltage could restore the oxidative properties of the solute, resulting in continuous removal of lignin. On the other hand, according to the oxidation pathway, the external voltage could promote the transformation of lignin dissolved by the electrolyte. Therefore, it is a challenge to search for an inexpensive and economical electrolyte.

SUMMARY

The primary object of the present disclosure is to provide a method for upgrading pyrolysis oil through seawater electrochemical pretreatment of biomass, i.e. a method for upgrading pyrolysis oil through electrochemical pretreatment of biomass by using seawater or its simulant as an electrolyte, so as to overcome the shortcomings and deficiencies of the prior art.

Another object of the present disclosure is to provide use of the method for upgrading pyrolysis oil through seawater electrochemical pretreatment of biomass.

In order to achieve the above objects, the present disclosure provides the following technical solutions:

Provided is a method for upgrading pyrolysis oil through seawater electrochemical pretreatment of biomass, comprising:

(1) electrochemical pretreatment: crushing and sieving a biomass raw material to obtain a crushed biomass raw material, adding the crushed biomass raw material to a salt solution, and mixing to be uniform to obtain a reactant mixture; performing an electrolytic reaction on the reactant mixture under conditions of stirring and an external voltage of 5-15 V for 2-8 hours to obtain a product mixture; after the electrolytic reaction, subjecting the product mixture to a suction filtration, collecting a filter cake, washing the filter cake and drying to obtain a pretreated biomass (which has an increased content of cellulose and reduced content of lignin), wherein the salt solution is seawater or a NaCl solution with a concentration of NaCl of 2-6.5% by mass; and (2) pyrolysis: subjecting the pretreated biomass obtained in step (1) to a pyrolysis reaction at a temperature of 400-600° C. for 30-90 minutes in a protective gas atmosphere to generate a pyrolysis oil, and collecting the pyrolysis oil by dissolving the pyrolysis oil in an organic solvent.

In some embodiments, the biomass raw material in step (1) is a conventional biomass raw material, such as a waste agricultural and forestry biomass raw material. In some embodiments, the biomass raw material in step (1) has relatively high content of cellulose and hemicellulose. In some embodiments, the biomass raw material in step (1) is a corn stalk.

In some embodiments, the crushing in step (1) is performed by a pulverizer.

In some embodiments, the sieving in step (1) is performed by a sieve with 40-200 meshes, preferably 80-100 meshes.

In some embodiments, the NaCl solution in step (1) has a concentration of NaCl of 2-5% by mass, preferably 2-3.5% by mass, more preferably 3.5% by mass (seawater in the world has an average concentration of NaCl of 35 g/Kg).

In some embodiments, a solid-to-liquid ratio of the biomass raw material to the salt solution in step (1) is in the range of 1 g:(100-150) mL, preferably 1 g: 100 mL. The above solid-to-liquid ratio could ensure that the solid biomass raw material and the salt solution are fully contacted.

In some embodiments, the stirring in step (1) is performed at 400-800 r/min for 10-40 minutes, preferably 600 r/min for 20 minutes. The purpose of the stirring is to make the biomass raw material fully react with the salt solution, which is beneficial to the reaction of intermediates produced by the electrolytic reaction with the biomass.

In some embodiments, in the electrochemical pretreatment in step (1), a graphite electrode (in some embodiments, the graphite electrode has a size of 6×95 mm) is used, and a distance between two electrodes (positive electrode and negative electrode) is 6 cm; the external voltage is provided by an adjustable direct current (DC) power supply; and the electrolytic reaction is performed in an undivided electrolytic tank.

In some embodiments, the electrolytic reaction in step (1) is carried out in a 800 mL glass electrolytic tank (taking a salt solution with a volume of 500 mL as an example). The electrolytic tank made of glass could prevent the damage of the electrolyte to the electrolytic tank; wherein, the electrolytic tank is an undivided electrolytic tank.

In some embodiments, the electrolytic reaction in step (1) is performed under an external voltage of 10-15 V, preferably 15 V.

In some embodiments, the electrolytic reaction in step (1) is performed at ambient temperature.

In some embodiments, the electrolytic reaction in step (1) is performed for 4-8 hours, preferably 8 hours.

In some embodiments, the washing in step (1) is performed by water, acetone and water sequentially until the filtrate is colorless and transparent.

In some embodiments, the drying in step (1) is performed at a temperature of 50-105° C., preferably 105° C.

In some embodiments, the drying in step (1) is performed for 5-24 hours, preferably 8 hours.

In some embodiments, the pyrolysis reaction in step (2) is carried out in a tube furnace. In some embodiments, the pyrolysis reaction is carried out in a quartz tube fixed bed reactor with a length of 500 mm and a diameter of 35 mm. In this reactor, the amount of the pretreated biomass is 0.5-2 g, preferably 0.5 g; and a quartz wool is placed at the bottom of the biomass, so that a pyrolysis bio-carbon is separated from the pyrolysis oil.

In some embodiments, the protective gas in step (2) is an inert gas. In some embodiments, the protective gas in step (2) is nitrogen gas. In some embodiments, the protective gas is introduced at a gas flow of 400-600 mL/min, preferably 550 mL/min. The protective gas is introduced at such a high gas flow in order to prevent the pyrolysis oil from repolymerizing in the pyrolysis reaction.

In some embodiments, the pyrolysis reaction in step (2) is performed at a temperature of 500° C.

In some embodiments, the collecting in step (2) is performed in a condensing device. In some embodiments, a condensing liquid used in the condensing device is industrial ethanol.

In some embodiments, the collecting in step (2) is performed at a condensation temperature of −10 to −20° C., preferably −18° C.

In some embodiments, the pyrolysis reaction in step (2) is performed for 30 minutes.

In some embodiments, the organic solvent in step (2) is acetone.

Provided is also use of the method for upgrading pyrolysis oil by seawater electrochemical pretreatment of biomass in preparation of pyrolysis oil, levoglucan and/or furfural.

Compared with the prior art, the embodiments of the present disclosure have the following advantages and effects:

(1) The present disclosure provides a pretreatment method of waste biomass (such as corn stalks), which makes it possible to adjust the composition and structure of the biomass, increase the content of cellulose in the biomass, reduce the content of lignin in the biomass, change the structure of the biomass to generate a new pore structure, and realize waste utilization owing to the low price of waste biomass raw materials.

(2) The present disclosure provides a method for electrochemical pretreatment of biomass (electrically assisted pretreatment with seawater), which could use seawater or its simulant, i.e. NaCl aqueous solution, as an electrolyte without other additional chemical reagents.

(3) The present disclosure provides a method for upgrading pyrolysis oil. The biomass is subjected to a pretreatment and a pyrolysis reaction, making the content of levoglucan in the pyrolysis oil increase from 0% to a maximum of 31.24% (at an external voltage of 15 V for 8 h), and the content of furfural increase from 4.03% to a maximum of 14.15% (at an external voltage of 15 V for 4 h). Therefore, the method according to the present disclosure could be used to prepare levoglucan and furfural.

BRIEF DESCRIPTION OF THE DRAWINGS

FIGS. 1A-1C show diagrams of a solid yield and lignocellulose composition obtained under different conditions of the electrochemical pretreatment, in which FIG. 1A shows a diagram of the solid yield and lignocellulose composition obtained under different external voltages; FIG. 1B shows a diagram of the solid yield and lignocellulose composition obtained under different time of the electrochemical pretreatment; and FIG. 1C shows a diagram of the solid yield and lignocellulose composition obtained under different salt concentrations.

FIGS. 2A-2C show diagrams of distribution of the pyrolysis oil obtained under different conditions of the electrochemical pretreatment, in which FIG. 2A shows a diagram of distribution of the pyrolysis oil obtained under different external voltages; FIG. 2B shows a diagram of distribution of the pyrolysis oil obtained under different time of the electrochemical pretreatment; and FIG. 2C shows a diagram of distribution of the pyrolysis oil obtained under different salt concentrations.

FIG. 3A-3C show diagrams of relative contents of typical compounds in the pyrolysis oil obtained under different conditions of the electrochemical pretreatment, in which FIG. 3A shows a diagram of relative contents of typical compounds obtained under different external voltages; FIG. 3B shows a diagram of relative contents of typical compounds obtained under different time of the electrochemical pretreatment; FIG. 3C shows a diagram of relative contents of typical compounds obtained under different salt concentrations.

FIG. 6A-6F show scanning electron microscope (SEM) images of the pretreated biomass obtained under different conditions of the electrochemical pretreatment, in which FIG. 6A shows a SEM image of an crude sample, in which FIG. 6B shows a SEM image of the pretreated biomass obtained at an external voltage of 5 V for 4 h; FIG. 6C shows a SEM image of the pretreated biomass obtained at an external voltage of 10 V for 4 h; and FIG. 6D shows a SEM image of the pretreated biomass obtained at an external voltage of 15 V for 4 h; FIG. 6E shows a SEM image of the seawater; and FIG. 6F shows a SEM image of the sample named 6.5%.

DETAILED DESCRIPTION OF THE EMBODIMENTS

Figure 1A:
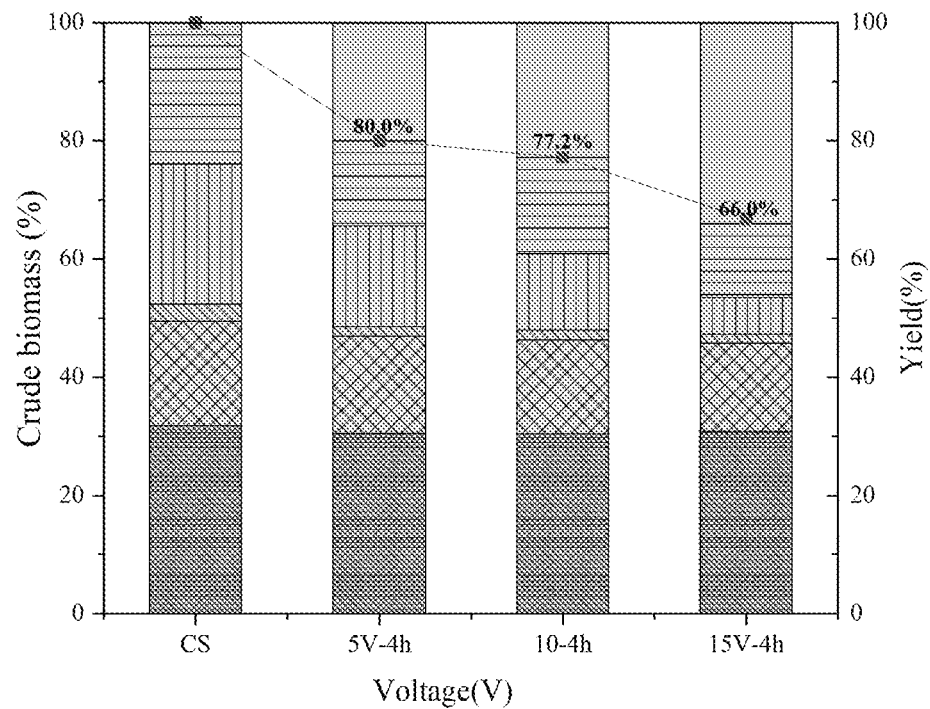

The present disclosure will be further described in detail below with reference to the examples, but the embodiments of the present disclosure are not limited thereto. Unless otherwise specified, the reagents, methods and equipment used in the present disclosure are conventional in the prior art. The test methods that do not specify specific experimental conditions in the following examples are usually carried out in accordance with conventional experimental conditions or in accordance with experimental conditions suggested by the manufacturer. Unless otherwise specified, the reagents and raw materials used in the present disclosure could be commercially available.

In the present disclosure, NaCl (Analytical reagent 99.5%) used in the examples was purchased from Shanghai Macklin Biochemical Co., Ltd., China.

In the present disclosure, the seawater used in the examples came from the coastal coral reef area, Weihai, Shandong Province, China.

In the present disclosure, the corn stalk used in the examples were purchased from Henan Province, China. The corn stalk was pretreated as follows: the corn stalk was crushed by a pulverizer, sieved by a sieve with 80-100 meshes, and dried at a temperature of 105° C. for 24 h to obtain a pretreated corn stalk. The pretreated corn stalk was collected in a sealed bag for subsequent pretreatment and pyrolysis experiments.

In the present disclosure, the pyrolysis oil obtained in the examples is tested by gas chromatography-mass spectrometry (GC-MS), and the content of target substance is calculated according to the following formula:

$$R_{target}\% = \frac{R_{target}}{R_1 + R_2 + \ldots + R_n} \times 100\%;$$

In the formula, $R_1, R_2, \ldots, R_n$ are GC-MS percentages (%) of each substance in a liquid-phase product.

The GC-MS test were conducted under conditions as follows:

The specific composition of the rapid pyrolysis oil was determined by Agilent 7890b-5977A gas chromatography-mass spectrometry equipped with a Ptx-Wax column (30.00 m×0.25 mm×0.25 μm). A temperature in an evaporator was set to be 280° C. A temperature of the column was controlled by a temperature program, and specifically, the temperature of the column was firstly controlled to be an initial temperature of 40° C. for 5 min, and increased to 150° C. at a rate of 10° C./min, then increased to a temperature of 200° C. at a rate of 5° C./min for 5 min, and finally increased to a temperature of 240° C. at a rate of 10° C./min for 8 min.

In the present disclosure, a two-step sulfuric acid (with a mass fraction of 72% and 4% respectively) hydrolysis method (based on the National Renewable Energy Laboratory (NREL) method of the United States) is adopted to determine the contents of lignin, cellulose and hemicellulose in the crude corn stalk and the corn stalks after the electrochemical pretreatment.

The solid yield is calculated as follows:

Solid yield (%)=the mass of remaining solids(g)/the mass of crude biomass(g)×100%;

Water Soluble Phase (%)=100%−Solid yield.

In order to eliminate the influence of impurities in seawater, a NaCl solution with a mass concentration of NaCl of 3.5 wt % is adopted in the present disclosure, which is used as a seawater simulant for electrochemical pretreatment (the seawater in the world has an average salt concentration of 35 g/Kg).

Example 1

Electrochemical pretreatment at different external voltages (1) 17.5 g of NaCl was weighted and put into an undivided electrolytic tank (a glass electrolytic tank with a volume of 800 mL was used to prevent damage to the electrolytic tank caused by the electrolyte), and then 500 mL of deionized water was added thereto. The undivided electrolytic tank was placed on an electronic stirrer and the materials therein were stirred at 600 r/min until there was no obvious NaCl crystal, to obtain a NaCl solution with a mass concentration of NaCl of 3.5 wt %. A corn stalk was crushed with a pulverizer, sieved and dried to obtain a biomass with 80-100 meshes. 5 g of the biomass was added into the undivided electrolytic tank, and the materials therein were stirred at a speed of 600 r/min for 20 minutes until they were mixed to be uniform to obtain a reactant mixture. Two 6×95 mm graphite electrodes were inserted into the undivided electrolytic tank, and the distance between the two electrodes (i.e. the gap between the two electrodes) was set to be 6 cm. An external voltage of 5 V, 10 V, and 15V was applied respectively for 4 hours through an adjustable DC power supply (MS3010DS). During this process, the reactant mixture was stirred continuously at a stirring speed of 600 r/min to obtain a product mixture. After the reaction, the obtained product mixture was subjected to a suction filtration to collect a filter cake, and then the filter cake was washed by water and filtrated by suction once, and then the filter cake after the suction filtration was washed by acetone (to wash away the degradation products during the biomass pretreatment process) and filtrated by suction, and then the resulting filter cake was washed by water until the filtrate was colorless and transparent and filtrated by suction to obtain a solid. The solid was dried in an oven at 105° C. for 8 hours to obtain an electrochemically pretreated sample. The electrochemically pretreated samples obtained at different voltages were named as 5 V4 h, 10 V-4 h, and 15 V-4 h, respectively. Further, an untreated corn stalk was used as a control, and was named as crude sample (CS).

(2) Each sample was subjected to a pyrolysis reaction in a tube furnace, specifically in a quartz tube fixed bed reactor with a length of 500 mm and a diameter of 35 mm. 0.5 g of each sample was placed in the middle of the fixed bed, and a quartz wool was placed at the bottom. To prevent the repolymerization of gaseous products, high-purity nitrogen gas was used as a protective gas, with a flow rate of 550 mL/min. When the tube furnace was heated to a temperature of 500° C., the quartz tube was quickly inserted into the tube furnace to conduct the pyrolysis reaction to produce a pyrolysis oil. The pyrolysis oil was condensed in a condensing device (with a condensing liquid of industrial ethanol) at a temperature of −18° C. The pyrolysis reaction was conducted for 0.5 hours. After the reaction, the quartz tube was taken out and cooled to ambient temperature. The pyrolysis oil was dissolved in acetone and then collected in a serum bottle.

Example 2

Electrochemical Pretreatment for Different Times (1) 17.5 g of NaCl was weighted and put into an undivided electrolytic tank (a glass undivided electrolytic tank with a volume of 800 mL), and then 500 mL of deionized water was added thereto. The undivided electrolytic tank was placed on an electronic stirrer and the materials therein were stirred at 600 r/min until there was no obvious NaCl crystal, to obtain a NaCl solution with a mass concentration of NaCl of 3.5 wt %. A corn stalk was crushed with a pulverizer, sieved and then dried to obtain a biomass with 80-100 meshes. 5 g of the biomass was added to the undivided electrolytic tank, and the materials therein were stirred at a speed of 600 r/min for 20 minutes until they were mixed to be uniform to obtain a reactant mixture. Two 6×95 mm graphite electrodes were inserted into the undivided electrolytic tank, and the distance between the two electrodes was set to be 6 cm. An external voltage of 15 V was applied for 2 hours, 4 hours, 6 hours and 8 hours respectively through an adjustable DC power supply (MS3010DS). During this process, the reactant mixture was stirred continuously at a stirring speed of 600 r/min to obtain a product mixture. After the reaction, the obtained product mixture was subjected to a suction filtration to collect a filter cake, and then the filter cake was washed by water and filtrated by suction once, and then the filter cake after the suction filtration was washed by acetone (to wash away the degradation products during the biomass pretreatment process) and filtrated by suction, and then the resulting filter cake was washed by water until the filtrate was colorless and transparent and filtrated by suction to obtain a solid. The solid was dried in an oven at 105° C. for 8 hours to obtain an electrochemically pretreated sample. The electrochemically pretreated samples obtained under different times were named as 15 V-2 h, 15 V-4 h, 15 V-6 h, and 15 V-8 h respectively.

(2) Each sample was subjected to a pyrolysis reaction in a tube furnace, specifically, in a quartz tube fixed bed reactor with a length of 500 mm and a diameter of 35 mm. 0.5 g of each sample was placed in the middle of the fixed bed, and a quartz wool was placed at the bottom. To prevent the repolymerization of gaseous products, high-purity nitrogen gas was used as a protective gas, with a flow rate of 550 mL/min. When the tube furnace was heated to a temperature of 500° C., the quartz tube was quickly inserted into the tube furnace to conduct the pyrolysis reaction to produce a pyrolysis oil. The pyrolysis oil was condensed in a condensing device (with a condensing liquid of industrial ethanol) at a temperature of −18° C. The pyrolysis reaction was conduct for 0.5 hours. After the reaction, the quartz tube was taken out and cooled to ambient temperature. The pyrolysis oil was dissolved in acetone and then collected in a serum bottle.

Example 3

Electrochemical pretreatment under different salt concentrations (1) 10 g, 17.5 g, 25 g, 32.5 g of NaCl was weighted and put into an undivided electrolytic tank (a glass electrolytic tank with a volume of 800 mL) respectively, and then 500 mL of deionized water was added thereto. The undivided electrolytic tank was placed on an electronic stirrer and the materials therein were stirred at 600 r/min until there was no obvious NaCl crystal, to obtain a NaCl solution with a mass concentration of NaCl of 2 wt %, 3.5 wt %, 5 wt % and 6.5 wt %, respectively. A corn stalk was crushed with a pulverizer, sieved and then dried to obtain a biomass with 80-100 meshes. 5 g of the biomass was added to the undivided electrolytic tank, and the materials therein were stirred at a speed of 600 r/min for 20 minutes until they were mixed to be uniform to obtain a reactant mixture. Two 6-95 mm graphite electrodes were inserted into the undivided electrolytic tank, and the distance between the two electrodes was set to be 6 cm. An external voltage of 15 V was applied for 4 hours through an adjustable DC power supply (MS3010DS). During this process, the reactant mixture was stirred continuously at a stirring speed of 600 r/min to obtain a product mixture. After the reaction, the obtained was subjected to a suction filtration to collect a filter cake, and then the filter cake product mixture was washed by water and filtrated by suction once, and then the filter cake after the suction filtration was washed by acetone (to wash away the degradation products during the biomass pretreatment reaction) and filtrated by suction, and then the resulting filter cake was washed by water until the filtrate was colorless and transparent and filtrated by suction to obtain a solid. The solid was dried in an oven at 105° C. for 8 hours to obtain an sample. The electrochemically pretreated samples obtained under different salt concentrations were named as 2%, 3.5%, 5% and 6.5%, respectively.

(2) Each sample was subjected to a pyrolysis reaction in a tube furnace, specifically in a quartz tube fixed bed reactor with a length of 500 mm and a diameter of 35 mm. 0.5 g of each sample was placed in the middle of the fixed bed, and a quartz wool was placed at the bottom. To prevent the repolymerization of gaseous products, high-purity nitrogen gas was used as a protective gas, with a flow rate of 550 mL/min. When the tube furnace was heated to a temperature of 500° C., the quartz tube was quickly inserted into the tube furnace to conduct the pyrolysis reaction to produce a pyrolysis oil. The pyrolysis oil was condensed in a condensing device (with a condensing liquid of industrial ethanol) at a temperature of −18° C. The pyrolysis reaction was conducted for 0.5 hours. After the reaction, the quartz tube was taken out and cooled to ambient temperature. The pyrolysis oil was dissolved in acetone and then collected in a serum bottle.

Example 4

Electrochemical Pretreatment by Using Real Seawater (1) 500 mL of seawater was added into an undivided electrolytic tank (a glass undivided electrolytic tank with a volume of 800 mL). A corn stalk was crushed with a pulverizer, sieved and then dried to obtain a biomass with 80-100 meshes. 5 g of the biomass was added to the undivided electrolytic tank, and the materials therein were stirred at a speed of 600 r/min for 20 minutes until they were mixed to be uniform to obtain a reactant mixture. Two 6×95 mm graphite electrodes were inserted into the undivided electrolytic tank, and the distance between the two electrodes was set to be 6 cm. An external voltage of 15 V was applied for 4 hours through an adjustable DC power supply (MS3010DS). During this process, the reactant mixture was stirred continuously at a stirring speed of 600 r/min to obtain a product mixture. After the reaction, the obtained product mixture was subjected to a suction filtration to collect a filter cake, and then the filter cake was washed by water and filtrated by suction once, and then the filter cake after the suction filtration was washed by acetone (to wash away the degradation products during the biomass pretreatment reaction) and filtrated by suction, and then the resulting filter cake was washed by water until the filtrate was colorless and transparent and filtrated by suction to obtain a solid. The solid was dried in an oven at 105° C. for 8 hours to obtain a seawater electrochemically pretreated sample. The seawater electrochemically pretreated sample was named as seawater (SW).

(2) The seawater electrochemically pretreated sample was subjected to a pyrolysis reaction in a tube furnace, specifically in a quartz tube fixed bed reactor with a length of 500 mm and a diameter of 35 mm. 0.5 g of the seawater electrochemically pretreated sample was placed in the middle of the fixed bed, and a quartz wool was placed at the bottom. To prevent the repolymerization of gaseous products, high-purity nitrogen gas was used as a protective gas, with a flow rate of 550 mL/min. When the tube furnace was heated to a temperature of 500° C. the quartz tube was quickly inserted into the tube furnace to conduct the pyrolysis reaction to produce a pyrolysis oil. The pyrolysis oil was condensed in a condensing device (with a condensing liquid of industrial ethanol) at a temperature of −18° C. The pyrolysis reaction was conducted for 0.5 hours. After the reaction, the quartz tube was taken out and cooled to ambient temperature. The pyrolysis oil was dissolved in acetone and then collected in a serum bottle.

Characterization Example

The contents of lignin, cellulose and hemicellulose, as well as the solid yield and water soluble phase in Examples 1 to 4 were measured according to the above methods. The pyrolysis oil collected in Examples 1-4 were tested by GC-MS. The results are shown in FIGS. 1A-6F and Table 1.

FIG. 1 shows the solid yield and lignocellulose composition obtained under different conditions of the electrochemical pretreatment. The contents of each component in corn stalk vary with different conditions of the electrochemical pretreatment.

As shown in FIG. 1A, the solid yield decreases from 80.0% to 66.0% as the voltage increases from 5 V to 15 V.

FIG. 1A also shows that different external voltages have little effect on the content of cellulose. After pretreatment, 95% of the cellulose is retained in the biomass. It is well known that lignin cross-links with cellulose and hemicellulose through covalent bonds and hydrogen bonds to form complex three-dimensional network structures. Therefore, some short-chain celluloses or oligosaccharides in the biomass are dissolved in water along with the degradation of lignin during electrochemical pretreatment. As shown in Table 1, with the increase of voltage, the relative content of cellulose increases from 31.78% to 46.71%, while the relative content of lignin decreases from 26.60% to 11.89%. The results indicate that electrochemical pretreatment by using seawater could effectively remove lignin.

TABLE 1

Composition of corn stalk and pretreated samples

| Chemical Components (%) | Crude sample | 5 V-4 h | 10-4 h | 15 V-4 h | 15 V-2 h | 15 V-6 h | 15 V-8 h | 2% | 5% | 6.5% | seawater |
|---|---|---|---|---|---|---|---|---|---|---|---|
| Lignin | 26.60 | 23.44 | 18.85 | 11.89 | 17.52 | 10.81 | 8.90 | 18.35 | 7.16 | 5.49 | 14.35 |
| Cellulose | 31.78 | 38.12 | 39.42 | 46.71 | 42.51 | 46.37 | 54.73 | 41.81 | 53.35 | 67.89 | 40.61 |
| Hemicellulose | 17.69 | 20.49 | 20.63 | 22.50 | 21.61 | 21.64 | 18.46 | 20.29 | 20.27 | 8.13 | 19.99 |
| Lignin removal rate | 0 | 29.49 | 45.29 | 70.50 | 49.67 | 75.46 | 83.46 | 49.64 | 86.43 | 92.86 | 63.53 |

Figure 1B:
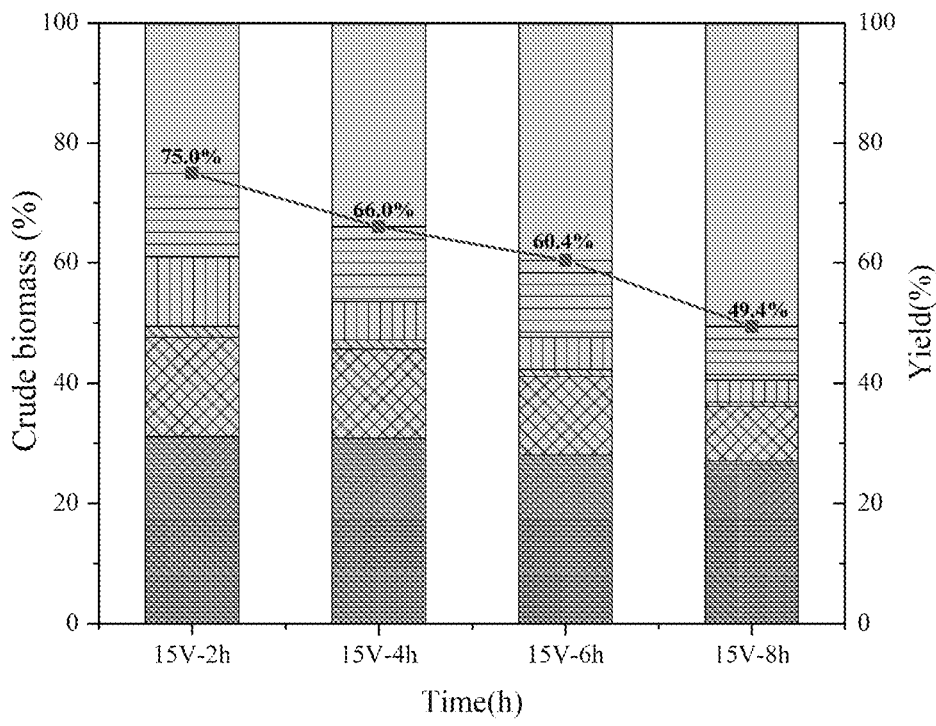
Figure 1C:
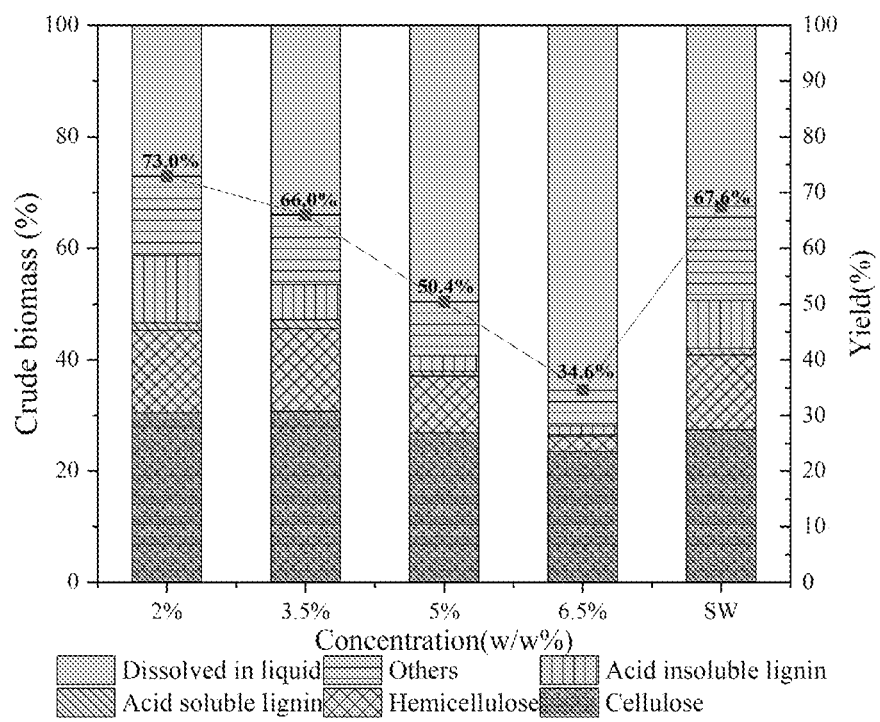

The time of electrochemical pretreatment has an important effect on solid yield. As shown in FIG. 1B, the solid yield of biomass decreases with the increase of the time of the electrochemical pretreatment. Especially when the time of the electrochemical pretreatment is increased from 2 hours to 8 hours, the relative content of lignin decreases from 17.52% to 8.90%, which is related to the attack of active Cl and OH* on lignin. Due to the removal of lignin after pretreatment, the relative content of hemicellulose increases from 21.61% to 22.50% and reaches a maximum at 4 hours.

In addition, the salt concentration also has an important effect on the electrochemical pretreatment. From FIG. 1C, a similar phenomenon could also be seen, specifically, when the concentration of the NaCl solution is increased to 6.5%, the content of hemicellulose decreases to 8.13%. This could be explained by the fact that during the electrochemical pretreatment, the higher the electrolyte concentration, the greater the current, the more thermal energy is generated to promote the hydrolysis of hemicellulose. Previous studies have shown that $ClO_2^-$ has a slight effect on hemicellulose, and it could be inferred that hemicellulose could be deconstructed by a group of $ClO_x^-$, and the group of $ClO_x^-$ has strong oxidative properties. With the increase of the concentration of the NaCl solution, more groups of $ClO_x^-$ are produced. Meanwhile, on the condition that lignin is destroyed, hemicellulose and cellulose are revealed. The group of $ClO_x^-$ reacts with hemicellulose and cellulose them in solution to convert them into small molecules soluble in water, which is not conducive to the enrichment of cellulose. Therefore, the concentration of the NaCl solution of around 3.5% is beneficial to the removal of lignin and the enrichment of cellulose and hemicellulose.

Figure 2A:
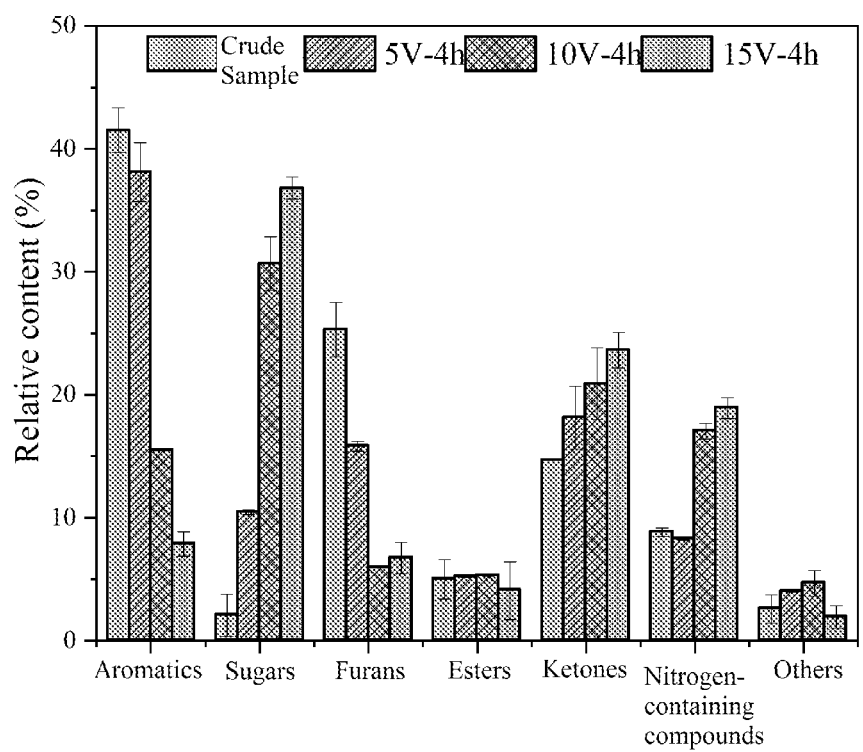
Figure 2B:
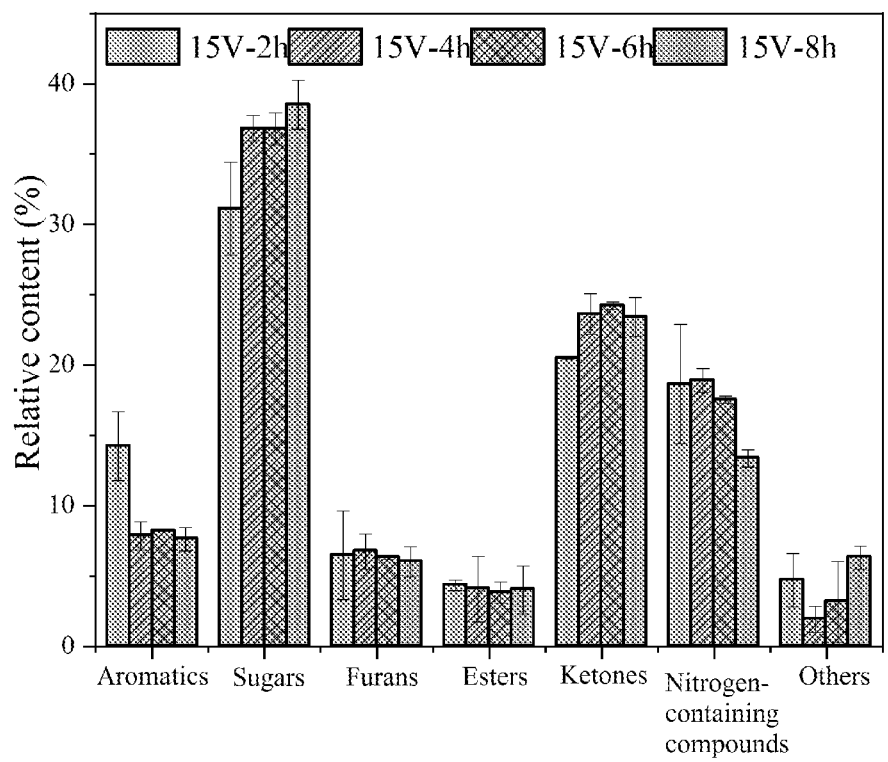

FIG. 2 shows distribution diagrams of the pyrolysis oil obtained under different pretreatment conditions.

As can be seen from FIG. 2A, the relative content of sugars in the pretreated samples increases significantly with the increase of the external voltage. At 5 V, 10 V and 15 V, the content of sugars increases from 2.07% to 10.46%. 30.69% and 36.82%, respectively. This result may be mainly attributed to the increase of the relative content of cellulose in the pretreated samples due to the decomposition of lignin under voltage, and the formation of porous structure after pretreatment which is conductive to the escape of sugar volatiles. In addition, the removal or passivation of alkaline earth metals would inhibit the ring-opening reaction of carbohydrates during pyrolysis, therefore the removal of alkaline earth metals in the pyrolysis oil is also considered to be a key factor to the content of sugars. The content of ketones increases from 14.68% to 18.14%, 20.90% and 23.64%, respectively. The aromatic hydrocarbons in the pyrolysis oil mainly come from the pyrolysis of lignin. The relative content of the aromatic hydrocarbons in the pyrolysis oil is 42.53%, 38.13%, 15.47% and 7.87%, corresponding to CS, 5V-4h, 10V-4h and 15V-4h samples respectively. The content of the aromatic hydrocarbons decreases significantly with the increase of the external voltage of the electrochemical pretreatment. The results show that with the increase of the external voltage of the electrochemical pretreatment, the relative content of lignin decreases from 26.60% to 11.89%, resulting in the reduction of aromatic hydrocarbons. The ash content decreases with the increase of the external voltage. Due to the catalytic effect of ash, the leaching of ash (ash is dissolved in water) leads to the reduction of volatile substances during the pyrolysis of lignin. In addition, due to the reduction of intermediate aromatic radicals generated by benzofuran, the content of furan decreases with the increase of the external voltage of the electrochemical pretreatment.

It can be concluded from the results that during the electrochemical pretreatment, the decomposition of lignin results in the decrease of the content of aromatic hydrocarbons with the increase of the time of the electrochemical pretreatment. However, with the prolongation of the time of the electrochemical pretreatment, the relative content of aromatic hydrocarbons remained at about 8% due to the rearrangement reaction of free radicals generated by cellulose. The contents of sugars and ketones increase with the increase of time of the electrochemical pretreatment, which is in line with changes in cellulose content (Table 1).

Figure 2C:
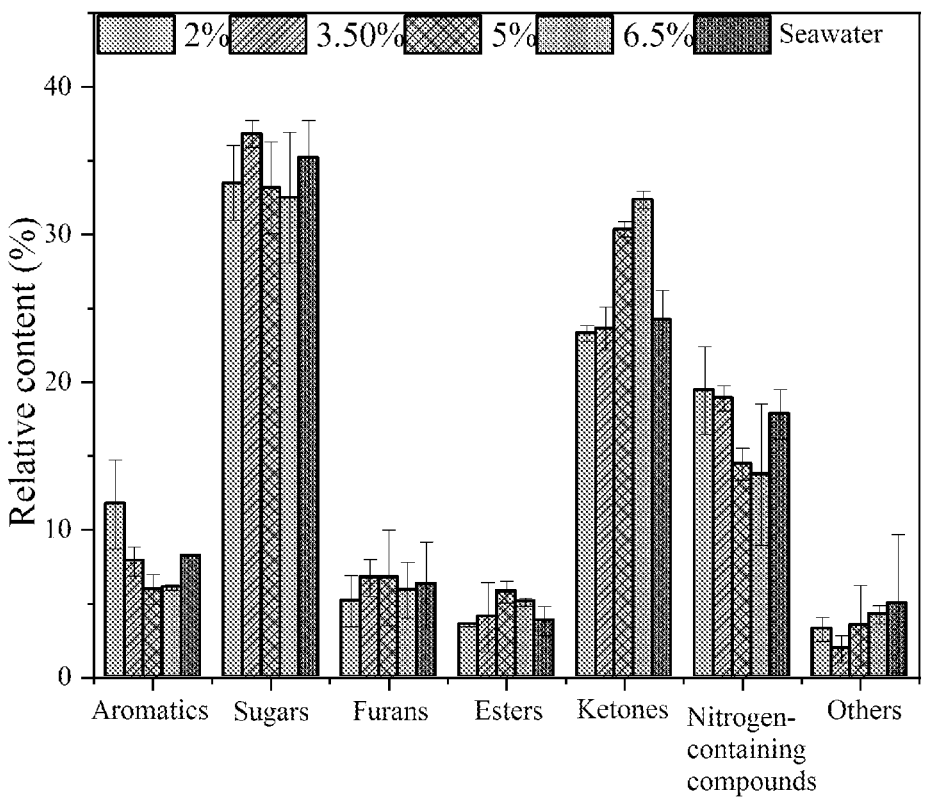

Furthermore, FIG. 2C shows diagrams of the distribution of the pyrolysis oil of samples obtained under different concentrations of the NaCl solution in the electrochemical pretreatment. The content of sugars fluctuates slightly between 33.18% and 36.83%. Especially for the pretreated corn stalk obtained by using real seawater in the electrochemical pretreatment, the content of sugars reaches 35.21%. For the corn stalk obtained under high concentrations of the NaCl solution in the electrochemical pretreatment, oxidized cellulose is formed, which may be detrimental to subsequent pyrolysis to produce sugars.

Figure 3A:
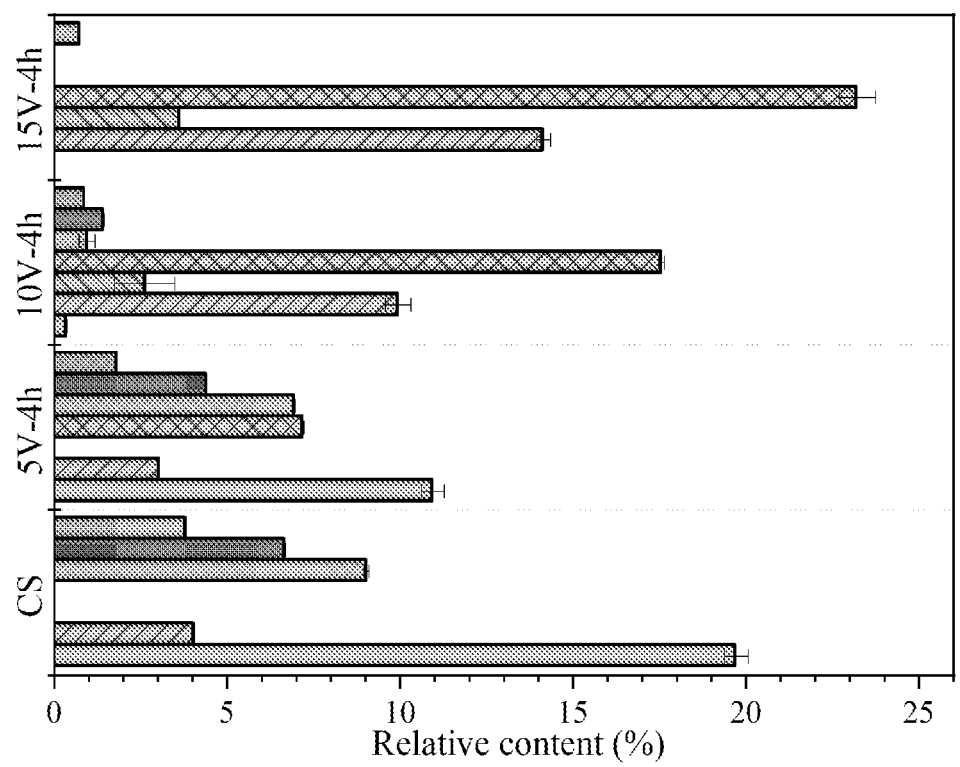
Figure 3B:
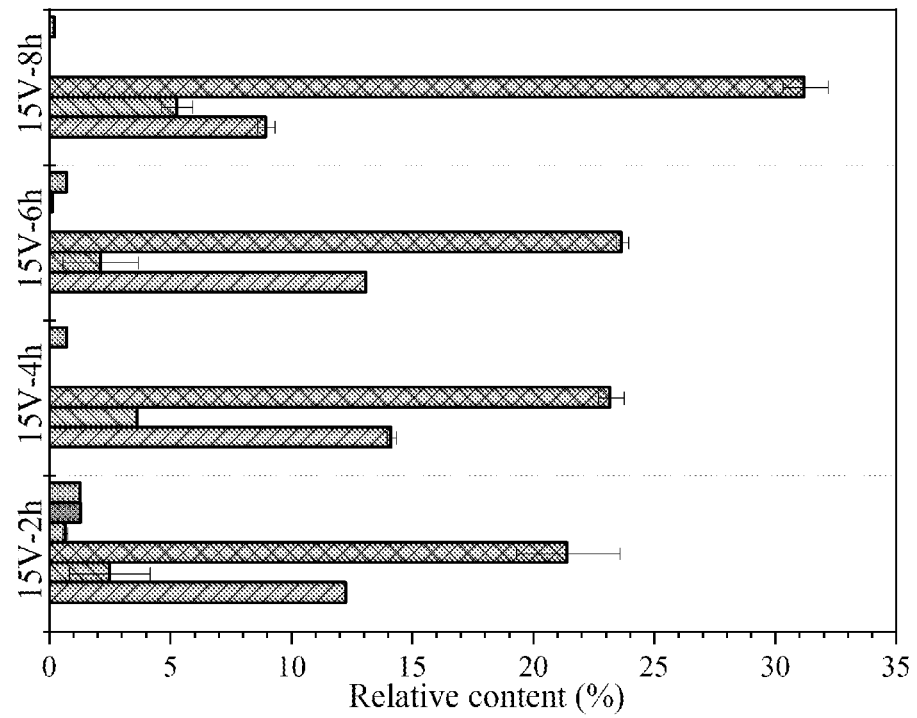
Figure 3C:
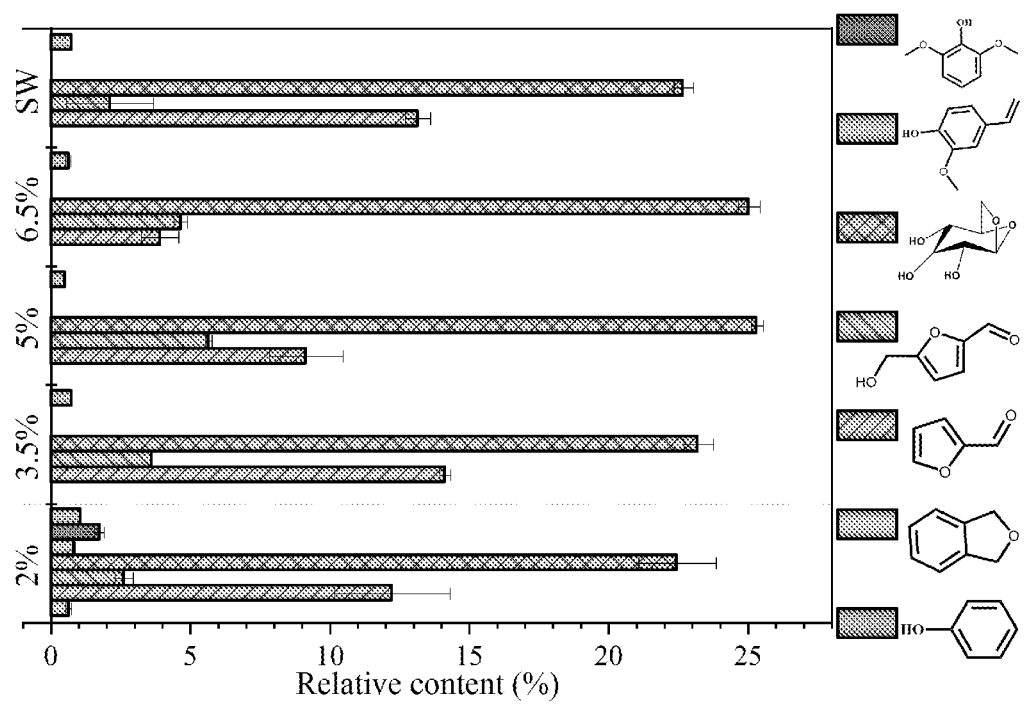
Figure 4:
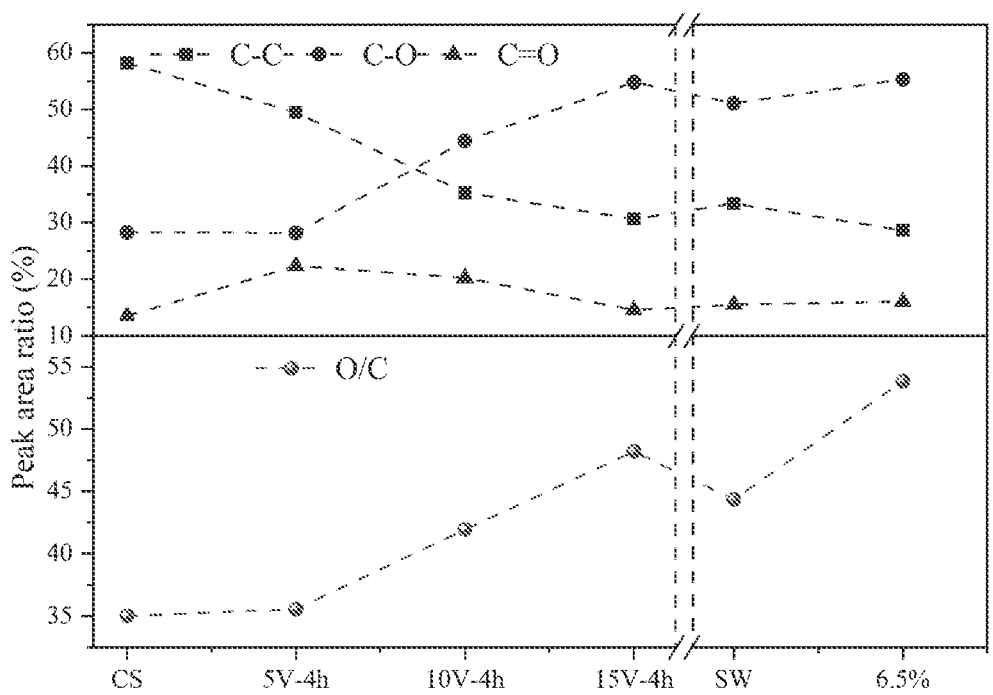
FIG. 4 shows a diagram of the results of X-ray photoelectron spectroscopy (XPS) analysis of the pretreated biomass obtained under different conditions of the electrochemical pretreatment.
Figure 5:
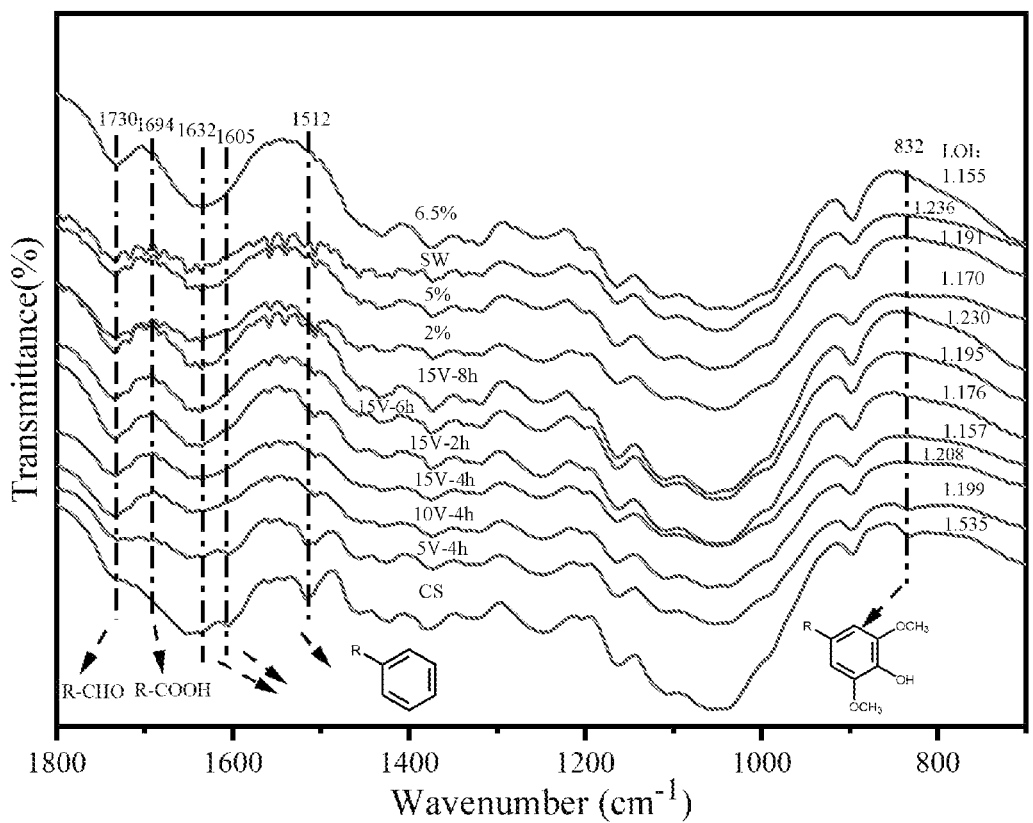
FIG. 5 shows a diagram of the results of Fourier transform infrared spectroscopy (FT-IR) analysis of the pretreated biomass obtained under different conditions of the electrochemical pretreatment.
Figure 6A:
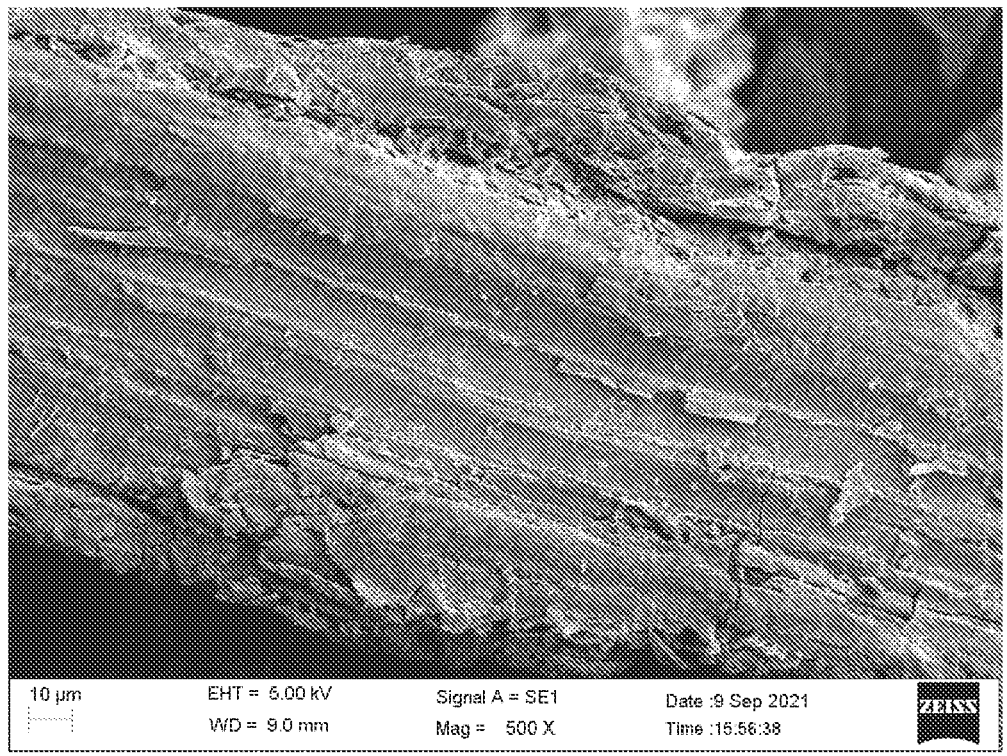
Figure 6B:
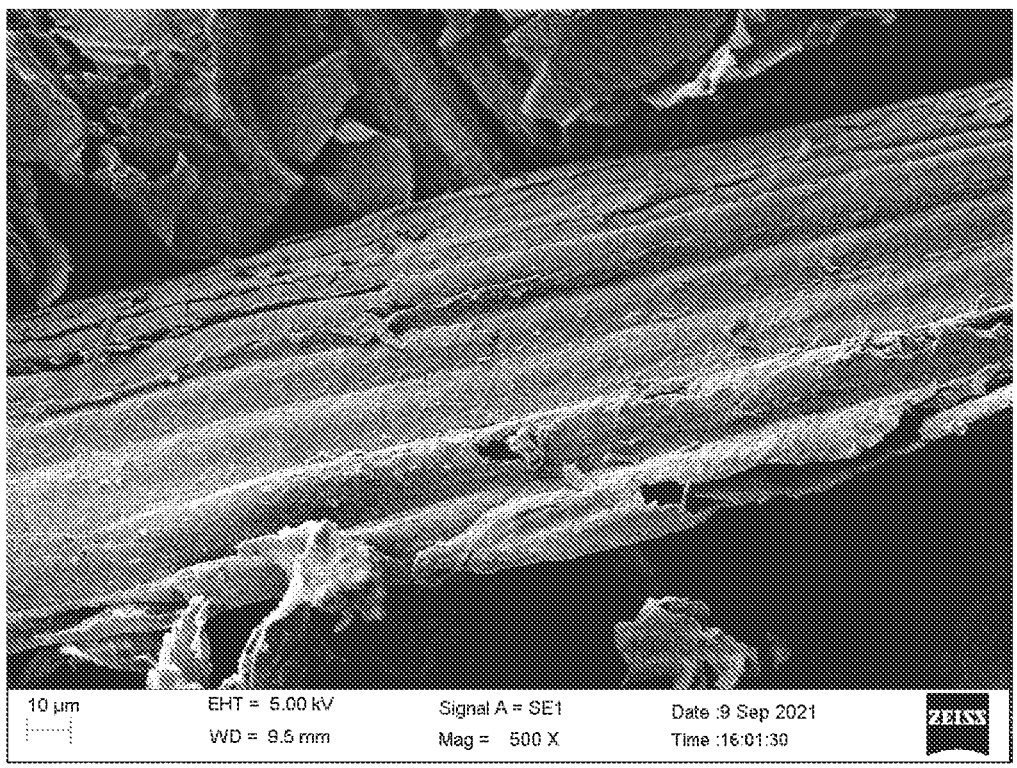
Figure 6C:
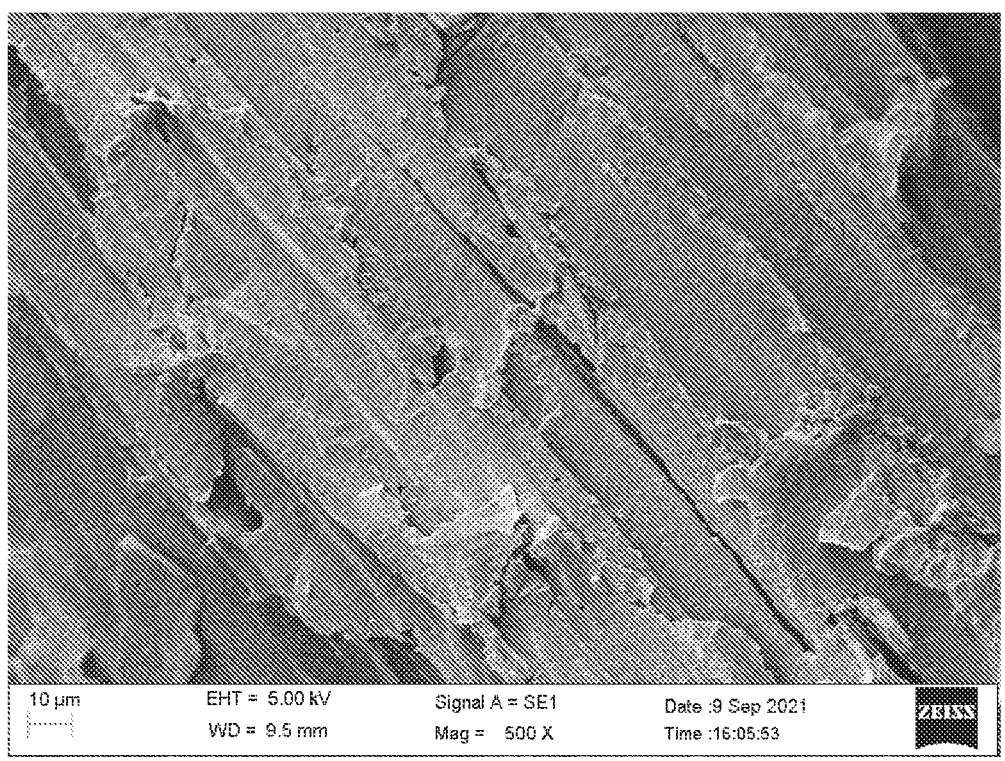
Figure 6D:
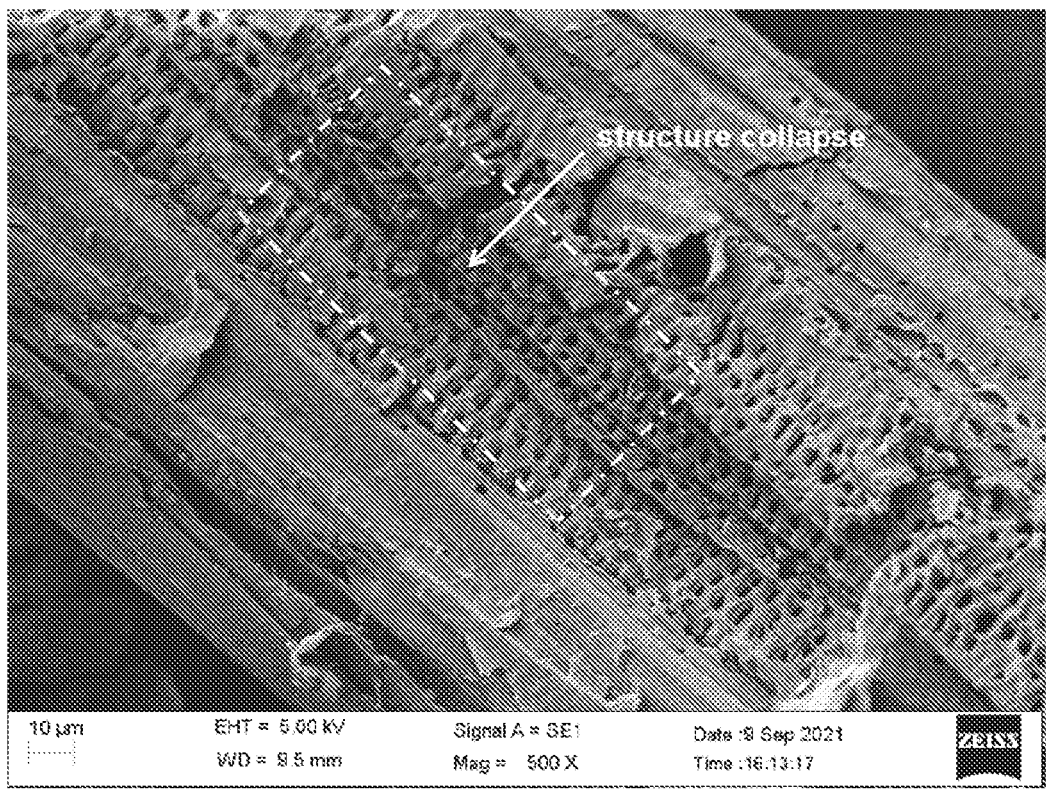
Figure 6E:
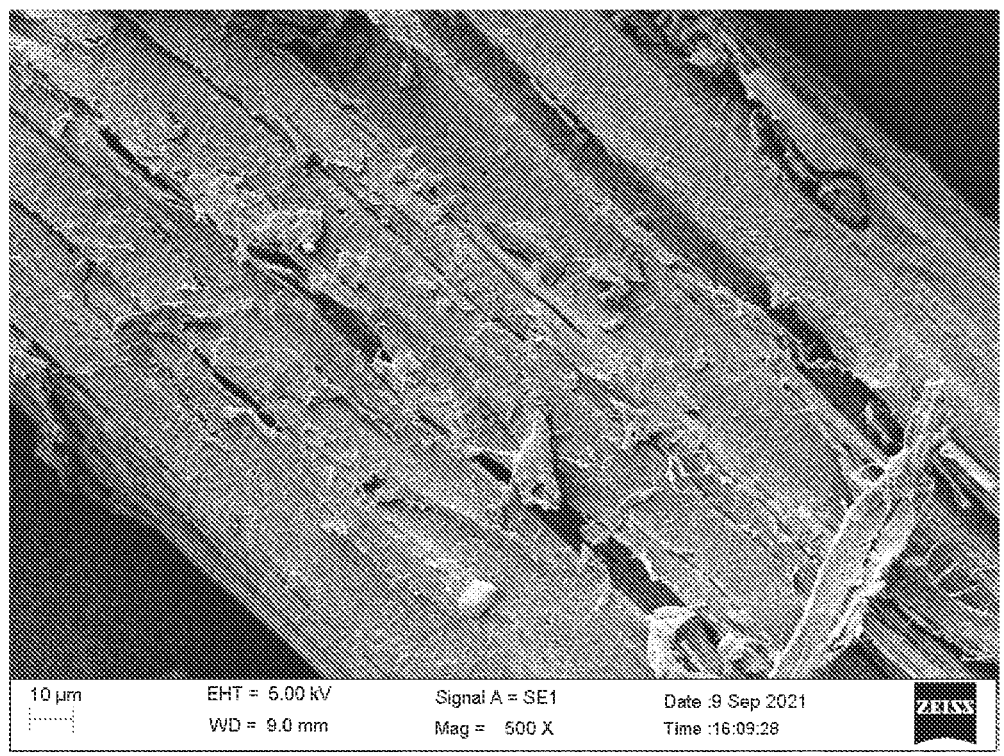
Figure 6F:
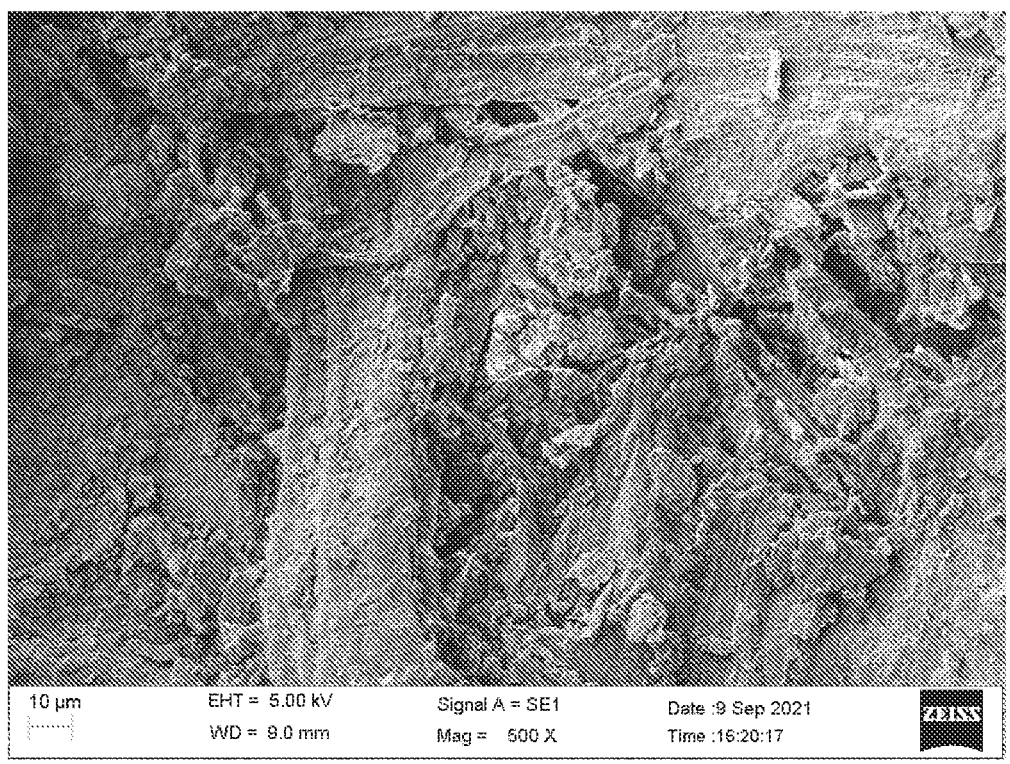

FIG. 3 shows the diagram of the relative contents of typical compounds obtained under different conditions of the electrochemical pretreatment. FIG. 4 and FIG. 5 show the diagram of XPS, and the diagram of FT-IR analysis of pretreated biomass obtained under different conditions of the electrochemical pretreatment, respectively. FIG. 6 shows SEM images of pretreated biomass obtained under different conditions of the electrochemical pretreatment.

The effect of the electrochemical pretreatment on typical compounds in the pyrolysis oil is shown in FIG. 3. During the pyrolysis of biomass, the main sugar produced by cleavage of cellulose glycosidic bonds is LG, and the reaction to form LG and the reaction to form 5-hydroxymethylfurfural are competing reactions. FIG. 3A shows that the content of LG and 5-hydroxymethylfurfural increase from 0% to 23.22% and 3.62%, respectively.

This is affected by several aspects as follows: 1) The ash is washed away during the electrochemical pretreatment while the ash is considered to play a catalytic role of catalyst in the rapid pyrolysis process. In the absence of the catalyst, the rapid quenching of volatile species would result in a product stream rich in anhydrosugar. 2) The analysis of XPS, FT-IR and SEM (FIG. 4, FIG. 5, and FIGS. 6A-6F) shows that the structure of lignin around the exterior of the cellulose is disrupted and the cellulose is exposed, thereby promoting the outward diffusion of sugars. After lignin is removed, the relative enrichment of cellulose results in higher content of LG in pyrolysis stream. 3) Due to the change of the pore structure on the surface of the biomass after pretreatment, the change of heat transfer coefficient and the escape route of volatile components also alter the pyrolysis yield of carbohydrates.

Likewise, the increase in the relative content of hemicellulose results in an increase in the content of furfural from 4.03% to 14.14%. The contents of 2-methoxy-4-vinylphenol and 2,6-dimethoxyphenol decrease from 9.03% and 6.66% respectively to 0% (which does not reach detection limit) relative to the content of lignin due to the lack of catalytic effect of ash on the pyrolysis and reduction of lignin. It is believed that o-quinone methide dissociates from other radicals by H-abstraction to form an intermediate of 2,3-benzofuran during the pyrolysis of biomass. Then, 2,3-benzofuran is reduced to be 2,3-dihydrobenzofuran. The decrease of intermediate free radicals results in a substantial decrease of 2,3-dihydrobenzofuran. After pretreatment, the aromatic hydrocarbons are greatly decreased; however, the rearrangement reaction during the pyrolysis of cellulose results in the constant presence of a certain amount of phenol in the pyrolysis oil. 5-hydroxymethylfurfural is the product of the depolymerization of cellulose, which could be converted to LG under certain conditions and vice versa. Therefore, the increase of the content of LG also leads to the increase of the content of 5-hydroxymethylfurfural. With the prolongation of pretreatment time and the increase of the concentration of the NaCl solution, the content of sugars increases to 31.25% and 25.04%, respectively. Due to the presence of Na, LG undergoes a ring-opening reaction during pyrolysis and is converted to other substances. Therefore, although the pretreated sample under high concentration of the NaCl solution in the electrochemical pretreatment has a content of cellulose higher than that of 15V-8h sample, it has less LG that is produced in the pyrolysis. Furthermore, dehydration reaction leads to the formation of dehydrated cellulose units, which are then converted to LG. However, the group of $ClO_x^-$ oxidizes the ends of characteristic chains of cellulose. The decrease of the ends of characteristic chains and the dehydrated cellulose units results in a decrease of the relative content of LG.

The above-mentioned examples are preferred embodiments of the present disclosure, but the embodiments of the present disclosure are not limited by the above-mentioned examples. Any other changes, modifications, substitutions, combinations, simplifications, made without departing from the spirit and principle of the present disclosure should be equivalent replacement methods, which are included within the protection scope of the present disclosure.

What is claimed is:

1. A method for upgrading pyrolysis oil through seawater electrochemical pretreatment of biomass, the method comprising:
   (1) a step of electrochemical pretreatment comprising:
      crushing and sieving a biomass raw material to obtain a crushed biomass raw material;

adding the crushed biomass raw material to a salt solution, and mixing the crushed biomass raw material and the salt solution to be uniform to obtain a reactant mixture;

performing an electrolytic reaction on the reactant mixture under conditions of stirring and an external voltage of 5-15 V for 2-8 hours to obtain a product mixture;

after the electrolytic reaction, subjecting the product mixture to a suction filtration, collecting a filter cake, washing the filter cake and drying to obtain a pretreated biomass, wherein the salt solution is seawater with a concentration of NaCl of 2-6.5% by mass or a NaCl solution with a concentration of NaCl of 2-6.5% by mass; and (2) a step of pyrolysis comprising:

subjecting the pretreated biomass obtained in step (1) to a pyrolysis reaction at a temperature of 400-600° C. for 30-90 minutes in a protective gas atmosphere, and collecting a pyrolysis oil by dissolving the pyrolysis oil in an organic solvent.

2. The method of claim 1, wherein
the seawater or the NaCl solution in step (1) has a concentration of NaCl of 2-5% by mass; and
a solid-to-liquid ratio of the biomass raw material to the salt solution in step (1) is in the range of 1 g: (100-150) mL.

3. The method of claim 2, wherein
the seawater or the NaCl solution in step (1) has a concentration of NaCl of 2-3.5% by mass; and
the solid-to-liquid ratio of the biomass raw material to the salt solution in step (1) is 1 g:100 mL.

4. The method of claim 3, wherein
the seawater or the NaCl solution in step (1) has a concentration of NaCl of 3.5% by mass.

5. The method of claim 1, wherein
the mixing in step (1) is performed at 400-800 r/min for 10-40 minutes;
the electrolytic reaction in step (1) is performed under an external voltage of 10-15 V;
the electrolytic reaction in step (1) is performed for 4-8 hours;
the pyrolysis reaction in step (2) is performed at a temperature of 500° C.;
the pyrolysis reaction in step (2) is performed for 30 minutes;
the collecting in step (2) is performed at a condensation temperature of −10 to −20° C.; and
the organic solvent in step (2) is acetone.

6. The method of claim 5, wherein
the mixing in step (1) is performed at 600 r/min for 20 minutes;
the electrolytic reaction in step (1) is performed under an external voltage of 15 V;
the electrolytic reaction in step (1) is performed for 8 hours; and
the collecting in step (2) is performed at a condensation temperature of −18° C.

7. The method of claim 1, wherein
the electrolytic reaction is performed using at least two graphite electrodes, wherein a distance between said at least two graphite electrodes is 6 cm;
the external voltage in step (1) is provided by a direct current power supply; and
the electrolytic reaction is performed in an undivided electrolytic tank.

8. The method of claim 1, wherein
the biomass raw material in step (1) is a waste agricultural and forestry biomass raw material;
the sieving in step (1) is performed by a 40-200 mesh sieve;
the washing in step (1) is performed using water, acetone and water sequentially;
the drying in step (1) is performed at a temperature of 50-105° C.;
the drying in step (1) is performed for 5-24 hours; and
the protective gas in step (2) is an inert gas.

9. The method of claim 8, wherein
the biomass raw material in step (1) is a corn stalk;
the sieving in step (1) is performed by an 80-100 mesh sieve;
the drying in step (1) is performed at a temperature of 105° C.;
the drying in step (1) is performed for 8 hours; and
the protective gas in step (2) is nitrogen gas, with a gas flow of 400-600 mL/min.

* * * * *

UNITED STATES PATENT AND TRADEMARK OFFICE
CERTIFICATE OF CORRECTION

| | | |
|---|---|---|
| PATENT NO. | : 11,732,196 B2 | Page 1 of 1 |
| APPLICATION NO. | : 17/851952 | |
| DATED | : August 22, 2023 | |
| INVENTOR(S) | : Xiwei Xu et al. | |

It is certified that error appears in the above-identified patent and that said Letters Patent is hereby corrected as shown below:

On the Title Page

Item (72) Inventors should read:
Xiwei Xu, Guangzhou (CN); Haipeng Yu, Guangzhou (CN); Enchen Jiang, Guangzhou (CN); Fan Zhang, Guangzhou (CN); Linghao Li, Guangzhou (CN); Hong Wang, Guangzhou (CN); Yan Sun, Guangzhou (CN)

Signed and Sealed this
Third Day of October, 2023

Katherine Kelly Vidal
*Director of the United States Patent and Trademark Office*